(12) United States Patent
He

(10) Patent No.: US 11,730,842 B2
(45) Date of Patent: *Aug. 22, 2023

(54) OZONE DISINFECTION DEVICE, OZONE DISINFECTION SYSTEM, AND OZONE DISINFECTION METHOD

(71) Applicant: DCSTAR INC, New York, NY (US)

(72) Inventor: Ligui He, New York, NY (US)

(73) Assignee: DCSTAR INC, New York, NY (US)

( * ) Notice: Subject to any disclaimer, the term of this patent is extended or adjusted under 35 U.S.C. 154(b) by 168 days.

This patent is subject to a terminal disclaimer.

(21) Appl. No.: 17/314,868

(22) Filed: May 7, 2021

(65) Prior Publication Data

US 2022/0016287 A1   Jan. 20, 2022

Related U.S. Application Data

(63) Continuation of application No. 16/931,157, filed on Jul. 16, 2020, now Pat. No. 11,000,611.

(51) Int. Cl.
*A61L 2/20* (2006.01)
*A61M 16/06* (2006.01)
*A61M 16/00* (2006.01)

(52) U.S. Cl.
CPC ......... *A61L 2/202* (2013.01); *A61M 16/0093* (2014.02); *A61M 16/0666* (2013.01); *A61L 2202/121* (2013.01); *A61L 2202/14* (2013.01); *A61L 2202/15* (2013.01); *A61L 2202/24* (2013.01)

(58) Field of Classification Search
CPC ... A61L 2/20; A61L 2/202; A61L 2/24; A61L 2202/122; A61L 2202/123; A61L 2202/13
USPC .................. 422/28, 30, 32–33, 305
See application file for complete search history.

(56) References Cited

U.S. PATENT DOCUMENTS

| | | | |
|---|---|---|---|
| 6,115,862 A | 9/2000 | Cooper et al. | |
| 9,981,052 B2 | 5/2018 | Clynne et al. | |
| 10,736,978 B2 | 8/2020 | Reiber et al. | |
| 10,842,907 B2 | 11/2020 | Goswami et al. | |
| 10,849,997 B2 | 12/2020 | Zhang et al. | |
| 11,000,611 B1 * | 5/2021 | He ............. | A61M 16/0666 |
| 2007/0166213 A1 * | 7/2007 | Miller ........... | A61L 2/202 |
| | | | 422/33 |
| 2016/0235876 A1 * | 8/2016 | Leyva ........... | A61L 2/202 |
| 2017/0151359 A1 | 6/2017 | Clynne et al. | |
| 2018/0055960 A1 | 3/2018 | Reiber et al. | |
| 2019/0046680 A1 | 2/2019 | Goswami et al. | |
| 2020/0114027 A1 | 4/2020 | Zhang et al. | |

* cited by examiner

*Primary Examiner* — Monzer R Chorbaji
(74) *Attorney, Agent, or Firm* — Hamre, Schumann, Mueller & Larson, P.C.

(57) ABSTRACT

The disclosure relates to disinfection application, particularly, to a device capable of disinfecting a ventilator as well as a face mask and a hose, and more particularly, to an ozone disinfection device, an ozone disinfection system, and an ozone disinfection method. An ozone disinfection device and an ozone disinfection system are provided. An ozone disinfection device includes: a sealed disinfection space, a gas distribution unit, an ozone generation unit, a suction pump, a filter, and a control module.

19 Claims, 7 Drawing Sheets

OZONE DISINFECTION DEVICE, OZONE DISINFECTION SYSTEM, AND OZONE DISINFECTION METHOD

TECHNICAL FIELD

The disclosure relates to the technical field of disinfection application, particularly, to a device capable of disinfecting a ventilator as well as a face mask and a hose, and more particularly, to an ozone disinfection device, an ozone disinfection system, and an ozone disinfection method.

BACKGROUND

At present, ozone disinfection methods are commonly used in the fields of medical equipment, catering tableware, food processing, etc. Ozone disinfection is highly efficient and economical. In ozone disinfection of items, items to be disinfected need to be placed in a sealed space, and ozone is fed into the sealed space to achieve disinfection. The ozone feeding space is relatively sealed, and high concentration of ozone is required to achieve full disinfection. As a result, after the items are disinfected, part of the ozone remains in the sealed space. For example, the ozone remains inside a ventilator or in a ventilator tube. The ozone cannot be completely eliminated in a short period of time, and when a user takes out the items, a pungent smell will be diffused. On the other hand, a large amount of ozone inhalation will also harm human health. At present, none of devices and products for ozone disinfection of a ventilator on the market actively recycle ozone. The characteristic of active elimination is that a device may actively recycle all the remaining ozone generated, so that all these ozone may be filtered through an ozone filter and catalytically decomposed, thereby achieving a safe and reliable effect. Unlike a passive technology, the passive technology refers to placing a filter at a certain position in a disinfection space and simply adsorbing ozone through the surface without an external force. The effect of this technology is not good and the efficiency is low, and only the ozone around the filter can be simply adsorbed while the ozone remaining in other spaces such as hoses cannot be effectively adsorbed.

The above content is only used to help understand the technical solutions of this application, and does not mean that the above content is recognized as the prior art.

SUMMARY

A technical problem to be solved by the disclosure is to provide an ozone disinfection device, which may quickly disinfect a ventilator as well as a face mask and a hose, and after disinfection is completed, it may efficiently pump remaining ozone out and evacuate after filtration of the ozone, to achieve high-speed elimination of the remaining ozone while not generating ozone pollution to the surrounding environment.

Another technical problem to be solved by the disclosure is to provide an ozone disinfection system.

Yet another technical problem to be solved by the disclosure is to provide another ozone disinfection system.

Still another technical problem to be solved by the disclosure is to provide an ozone disinfection method.

In order to solve the above technical problems, the technical solution adopted by the disclosure is to provide an ozone disinfection device, which includes:

a sealed disinfection space configured to receive a device to be disinfected or temporarily store ozone, the sealed disinfection space communicating with a through hole for allowing the insertion of a gas outlet end of the device to be disinfected;

a gas distribution unit including a first interface, a second interface, and a third interface that communicate with each other, the second interface being configured to communicate with a gas inlet end of the device to be disinfected;

an ozone generation unit having an ozone outlet communicating with the first interface, the ozone generation unit including an ozone generator configured to generate ozone and a power apparatus configured to deliver the ozone to the first interface;

a suction pump having a suction port and an exhaust port, the suction port communicating with the third interface;

a filter having a plurality of exhaust holes and at least one gas inlet, the gas inlet of the filter communicating with the exhaust port of the suction pump; and a control module configured to connect and control the operation of the ozone generation unit and the suction pump.

By using the ozone disinfection device in the above technical solution, when disinfecting a ventilator and a face mask and a hose thereof, the ventilator communicates with the second interface, after the sealed disinfection space is opened, the hose is inserted into the sealed disinfection space from the through hole, the face mask is put into the sealed disinfection space, the ventilator, the hose, and the face mask are connected in sequence, and then the sealed disinfection space is closed. After the above operations are completed, the control module activates the ozone generation unit, and ozone generated by the ozone generation unit flows into the ventilator, the hose, the face mask, and the sealed disinfection space in sequence through the gas distribution unit, thereby performing ozone disinfection treatment on the ventilator, the hose, and the face mask. After the disinfection is completed, the control module controls the ozone generation unit to stop working and activates the suction pump, the suction pump generates a strong negative pressure and pumps all the ozone remaining inside the sealed disinfection space, the face mask, the hose, and the ventilator to the filter, and the filter performs catalytic decomposition treatment on the ozone flowing through and then evacuates, thereby eliminating the ozone remaining inside the sealed disinfection space, the ventilator, the hose, and the face mask, and protecting a user from inhaling the remaining ozone when using the disinfected ventilator, hose and face mask while not causing ozone pollution to the surrounding environment. The safety and environmental protection of the ozone disinfection device are improved. Compared with existing passive ozone disinfection technologies, the ozone disinfection device has the advantages of higher efficiency, high speed, safety, and environmental protection.

In addition, the power apparatus may quickly expel the ozone generated by the ozone generator into the second interface, that is, the ozone generated by the ozone generator does not enter the second interface through a slow diffusion process, thus improving the work efficiency of the entire ozone disinfection device.

As an improvement of the ozone disinfection device provided by the disclosure, the filter includes a hollow housing, the housing has the plurality of exhaust holes and the gas inlet, the gas inlet is provided on lower sides of the plurality of exhaust holes, at least one filter layer is disposed between the gas inlet and the exhaust holes, and the housing internally has a buffer cavity that is located on a lower side of the lowermost filter layer and communicates with the gas inlet of the filter. Through the above improvement, since the filter has a plurality of exhaust holes, non-polluting gas generated by the catalytic decomposition of ozone may be expelled more quickly, thus improving the ventilation efficiency of the filter. In addition, considering that solid particles such as fine dust may be included in fast-flowing ozone gas, a buffer cavity is designed inside the housing, which functions to collect the solid particles included in the ozone gas for centralized removal.

As an improvement of the ozone disinfection device provided by the disclosure, two filter layers are disposed between the gas inlet and the exhaust holes, and there is a gap between the two filter layers. Through the above improvement, the catalytic ozone decomposition ability and efficiency of the filter are improved to ensure that no ozone is included in the gas expelled from the filter.

As an improvement of the ozone disinfection device provided by the disclosure, at least one of the filter layers is filled with manganese-containing particulate matters for catalytic ozone decomposition. Through the above improvement, the ozone flowing through the filter is decomposed into non-toxic and non-polluting oxygen under the action of the particulate matters to ensure the sanitation and safety of the surrounding environment.

As an improvement of the ozone disinfection device provided by the disclosure, the ozone disinfection device includes a base. The ozone generation unit, the suction pump, and the filter are all fixed on the base. The sealed disinfection space is located on upper sides of the ozone generation unit, the suction pump, and the filter. The sealed disinfection space is opened and closed in a flip type or a drawer type. Through the above improvement, an internal space of the ozone disinfection device is fully utilized, making the entire ozone disinfection device miniaturized and enhancing its portability.

As an improvement of the ozone disinfection device provided by the disclosure, the control module includes a display screen for displaying work progress and work content. The work progress includes a percentage of a total work time or a countdown of a work time. Through the above improvement, a user can better understand the work progress and work content of the ozone disinfection device.

As an improvement of the ozone disinfection device provided by the disclosure, the control module is configured to control the ozone generation unit to output enough ozone so that the concentration of ozone in the sealed disinfection space is not lower than a concentration value capable of killing conventional germs inside the ventilator. Through the above improvement, it is ensured that the ozone generation unit generates enough ozone in the disinfection process, and it is ensured that germs in the ventilator, the hose, and the face mask can be completely killed.

As an improvement of the ozone disinfection device provided by the disclosure, the suction volume of the suction pump is not lower than the exhaust volume of the ozone generation unit. Through the above improvement, the efficiency of eliminating the remaining ozone is further improved.

As an improvement of the ozone disinfection device provided by the disclosure, the ozone generation unit communicates with the first interface of the gas distribution unit through a first pipeline, the suction port of the suction pump communicates with the third interface of the gas distribution unit through a third pipeline, the exhaust port of the suction pump communicates with the gas inlet of the filter through a fourth pipeline, and the second interface of the gas distribution unit communicates with the gas inlet end of the device to be disinfected through a second pipeline. The material of the first pipeline, the second pipeline, the third pipeline, and the fourth pipeline is silica gel or Ethylene Propylene Diene Monomer.

In order to solve the above another technical problem, the technical solution adopted by the disclosure is to provide an ozone disinfection system, which includes: a ventilator, a hose, a face mask, and the ozone disinfection device as described above.

The ventilator, the hose, and the face mask communicate in sequence.

A gas inlet end of the ventilator communicates with the second interface of the gas distribution unit of the ozone disinfection device through a second pipeline.

A gas outlet end of the hose extends into the sealed disinfection space from the through hole.

The face mask is received in the sealed disinfection space.

In the ozone disinfection system provided by the disclosure, the control module is configured to control the ozone generation unit to output enough ozone so that the concentration of ozone in the sealed disinfection space is not lower than a concentration value capable of killing conventional germs inside the ventilator.

In the ozone disinfection system provided by the disclosure, the suction volume of the suction pump is not lower than the exhaust volume of the ozone generation unit.

In the ozone disinfection system provided by the disclosure, the sealed disinfection space is opened and closed in a flip type or a drawer type.

In the ozone disinfection system provided by the disclosure, the ozone generation unit communicates with the first interface of the gas distribution unit through a first pipeline, the suction port of the suction pump communicates with the third interface of the gas distribution unit through a third pipeline, the exhaust port of the suction pump communicates with the gas inlet of the filter through a fourth pipeline, and the second interface of the gas distribution unit communicates with the ventilator through the second pipeline.

In order to solve the above yet another technical problem, the technical solution adopted by the disclosure is to provide an ozone disinfection system, which includes: a hose, a face mask, and the ozone disinfection device as described above.

The hose and the face mask communicate with each other.

A gas inlet end of the hose communicates with the second interface of the gas distribution unit of the ozone disinfection device through a second pipeline.

A gas outlet end of the hose extends into the sealed disinfection space from the through hole.

The face mask is received in the sealed disinfection space.

In the ozone disinfection system provided by the disclosure, the control module is configured to control the ozone generation unit to output enough ozone so that the concentration of ozone in the sealed disinfection space is not lower than a concentration value capable of killing conventional germs inside a ventilator.

In the ozone disinfection system provided by the disclosure, the suction volume of the suction pump is not lower than the exhaust volume of the ozone generation unit.

In the ozone disinfection system provided by the disclosure, the sealed disinfection space is opened and closed in a flip type or a drawer type.

In the ozone disinfection system provided by the disclosure, the ozone generation unit communicates with the first interface of the gas distribution unit through a first pipeline, the suction port of the suction pump communicates with the third interface of the gas distribution unit through a third pipeline, the exhaust port of the suction pump communicates with the gas inlet of the filter through a fourth pipeline, and the second interface of the gas distribution unit communicates with the hose through the second pipeline.

In order to solve the above still another technical problem, the technical solution adopted by the disclosure is to provide an ozone disinfection method. The ozone disinfection method is implemented through the ozone disinfection device as described above. The ozone disinfection method includes the following steps:

connecting a gas outlet end and a gas inlet end of a device to be disinfected to the sealed disinfection space and the second interface, respectively;

activating, by the control module, the ozone generation unit, ozone generated by the ozone generation unit flowing into the device to be disinfected and the sealed disinfection space in sequence through the gas distribution unit;

controlling, by the control module, the ozone generation unit to stop working and activating the suction pump, generating, by the suction pump, a strong negative pressure, and pumping all the ozone remaining inside the sealed disinfection space and the device to be disinfected to the filter; and performing, by the filter, catalytic decomposition treatment on the ozone flowing through, and then evacuating.

In the ozone disinfection method provided by the disclosure, the ozone generation unit outputs a certain amount of ozone so that the concentration of ozone in the sealed disinfection space is not lower than a concentration value capable of killing conventional germs inside a ventilator.

Compared with the prior art, the implementation of the disclosure may achieve the following beneficial effects.

1. The ozone disinfection device may perform ozone disinfection treatment on a ventilator, a hose, and a face mask, and may also pump all the ozone remaining inside the sealed disinfection space, the face mask, the hose, and the ventilator to the filter, and the filter performs catalytic decomposition treatment on the ozone flowing through and then evacuates, thereby eliminating the ozone remaining inside the sealed disinfection space, the ventilator, the hose, and the face mask, and protecting a user from inhaling the remaining ozone when using the disinfected ventilator, hose and face mask while not causing ozone pollution to the surrounding environment. The safety and environmental protection of the ozone disinfection device are improved. Compared with existing passive ozone disinfection technologies, the ozone disinfection device has the advantages of higher efficiency, high speed, safety, and environmental protection.

2. The ozone generation unit includes an ozone generator configured to generate ozone and a power apparatus configured to deliver the ozone to the first interface. The power apparatus may quickly expel the ozone generated by the ozone generator into the second interface, that is, the ozone generated by the ozone generator does not enter the second interface through a slow diffusion process, thus improving the work efficiency of the entire ozone disinfection device.

3. Since the filter has a plurality of exhaust holes, non-polluting gas generated by the catalytic decomposition of ozone may be expelled more quickly, thus improving the ventilation efficiency of the filter. In addition, considering that solid particles such as fine dust may be included in fast-flowing ozone gas, a buffer cavity is designed inside the housing, which functions to collect the solid particles included in the ozone gas for centralized removal.

BRIEF DESCRIPTION OF THE DRAWINGS

In order to more clearly explain the embodiments of the disclosure or the technical solutions in the prior art, the drawings to be used in the description of the embodiments or the prior art will be briefly introduced below. Obviously, the drawings in the following description are only some embodiments of the disclosure. For those of ordinary skill in the art, other drawings may be obtained according to the structures shown in these drawings without any creative work.

DESCRIPTION OF DRAWING REFERENCE NUMBER

Figure 1:
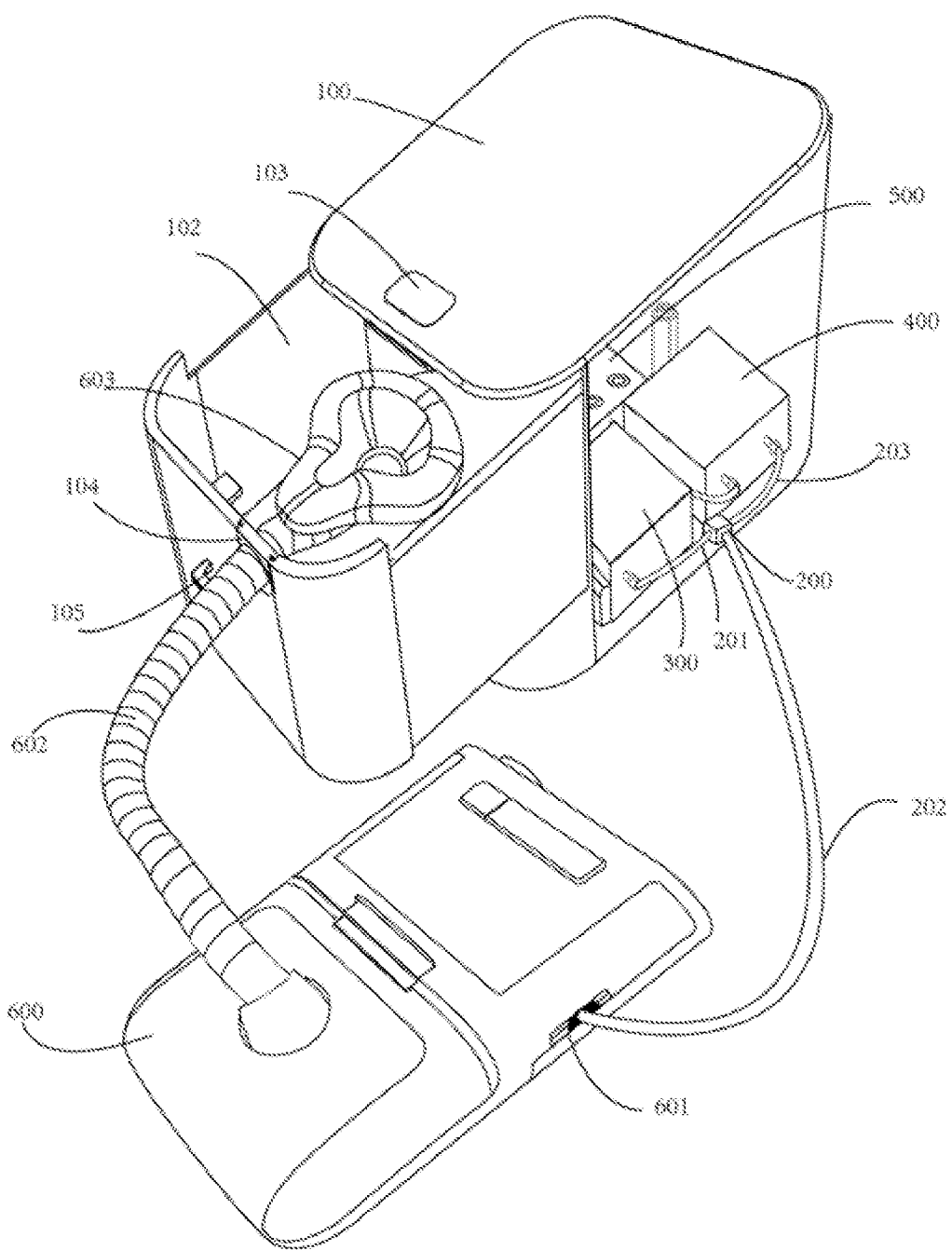
FIG. 1 is reference diagram (I) of a use state of an ozone disinfection device provided in Embodiment I of the disclosure, which illustrates a state in which the ozone disinfection device disinfects a ventilator, a hose, and a face mask.

| Name | Reference Number | Name | Reference Number |
|---|---|---|---|
| Ozone disinfection device | 100 | Base | 101 |
| Sealed disinfection space | 102 | Open button | 103 |
| Through hole | 104 | Gas distribution unit | 200 |
| First pipeline | 201 | Second pipeline | 202 |
| Third pipeline | 203 | Fourth pipeline | 204 |
| Ozone generation unit | 300 | Ozone outlet | 301 |
| Suction pump | 400 | Suction port | 401 |
| Exhaust port | 402 | Filter | 500 |
| Gas inlet | 501 | Exhaust hole | 502 |
| Buffer cavity | 503 | Filter layer | 504 |
| Ventilator | 600 | Gas inlet end | 601 |
| Hose | 602 | Face mask | 603 |
| Control module | 700 | Handle | 105 |

The implementation, functional characteristics, and advantages of the disclosure will be further described in conjunction with the embodiments and with reference to the drawings.

DETAILED DESCRIPTION

The technical solutions in the embodiments of the disclosure will be described below clearly and completely with reference to the drawings in the embodiments of the disclosure. Obviously, the described embodiments are only a part of the embodiments of the disclosure, but not all the embodiments. Based on the embodiments of the disclosure, all other embodiments obtained by a person of ordinary skill in the art without creative efforts fall within the scope of protection of the disclosure.

It should be noted that if there is a directional indicator (such as up, down, left, right, front, back . . . ) in the embodiments of the disclosure, the directional indicator is only used to explain contents including a relative positional relationship and movement of components in a specific posture (as shown in the drawings). If the specific posture changes, the directional indicator will also change accordingly.

In addition, if there are descriptions related to "first," "second," etc. in the embodiments of the disclosure, the descriptions of "first," "second," etc. are for descriptive purposes only, and cannot be understood as indicating or implying its relative importance or implicitly indicating the number of technical features indicated. Therefore, the features defined with "first" and "second" may include at least one of the features explicitly or implicitly. In addition, the meaning of "and/or" appearing throughout the text is to include three parallel solutions. For example, "A and/or B" includes a solution A, or a solution B, or a solution that A and B satisfy at the same time. In addition, the technical solutions between the various embodiments may be combined with each other, but it must be based on that the technical solutions can be achieved by those of ordinary skilled in the art. When the combination of the technical solutions is self-contradictory or cannot be achieved, it should be considered that such combination of the technical solutions neither exist, nor is within the scope of protection required by the disclosure.

Embodiment I

The present embodiment provides an ozone disinfection device 100. The ozone disinfection device 100 is particularly suitable for disinfecting a ventilatory apparatus. The ventilatory apparatus includes a ventilator 600, a hose 602, and a face mask 603 that communicate in sequence. It can be understood that the ventilator 600 and the face mask 603 are connected by the hose 602, the ventilator 600 and the hose 602 are of a detachable connection structure, and the face mask 603 and the hose 602 are of a detachable connection structure.

Figure 3:
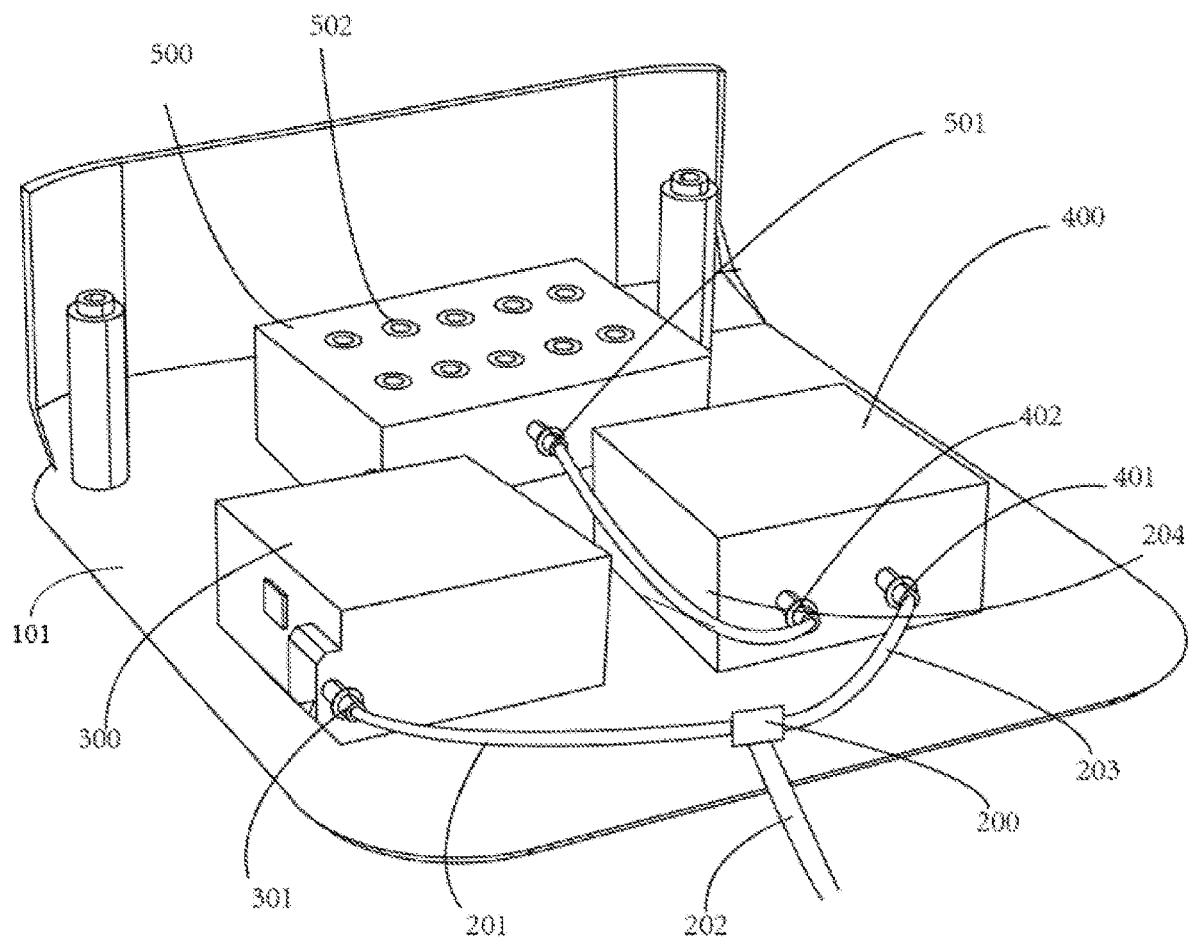
FIG. 3 is a schematic diagram of an internal structure of an ozone disinfection device provided in Embodiment I of the disclosure.
Figure 7:
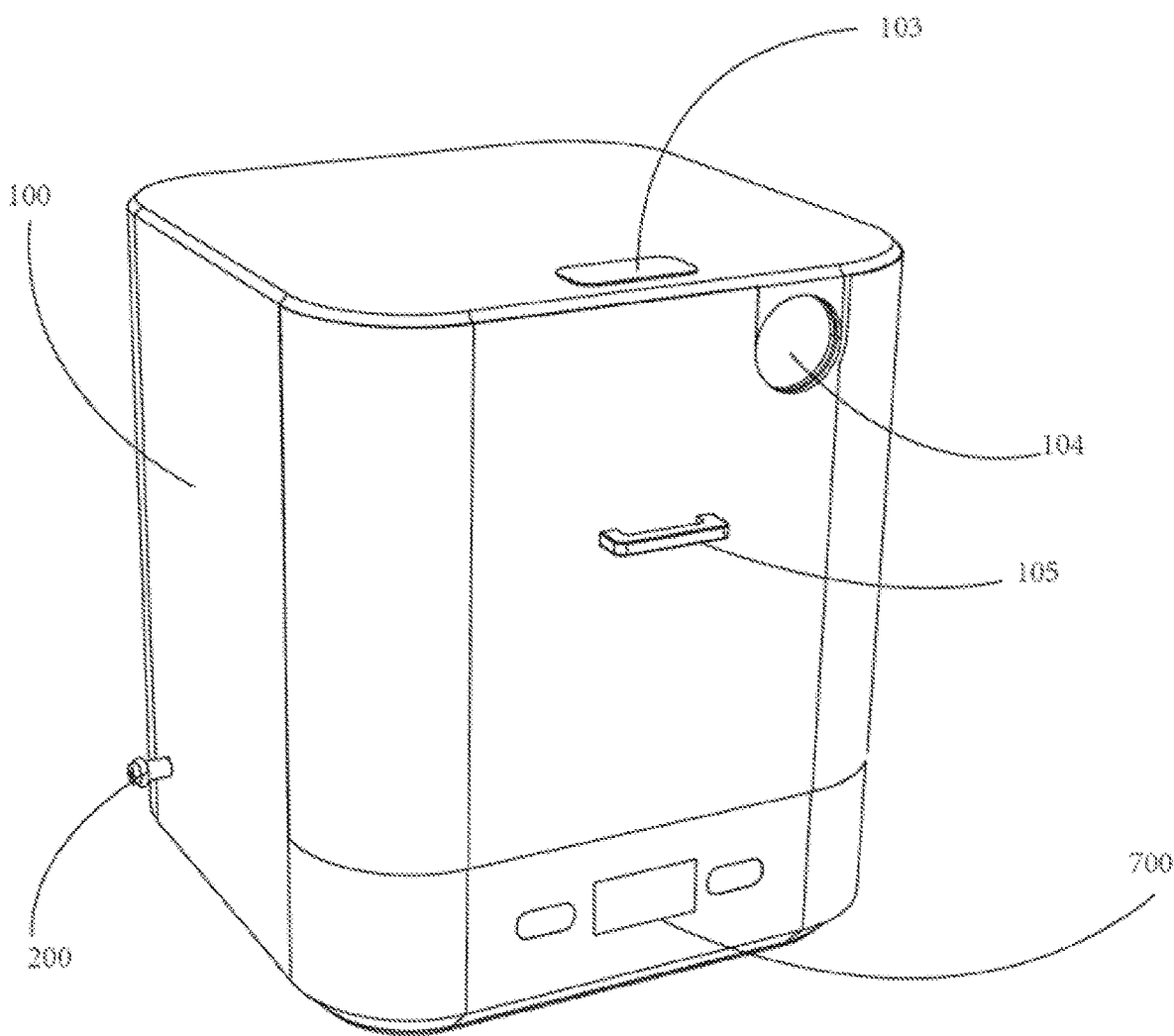
FIG. 7 is a schematic diagram of a three-dimensional structure of an ozone disinfection device provided in Embodiment I of the disclosure.

In the present embodiment, referring to FIG. 1, FIG. 3, and FIG. 7, the ozone disinfection device 100 includes: a sealed disinfection space 102 configured to receive a device to be disinfected or temporarily store ozone, the sealed disinfection space 102 communicating with a through hole 104, the through hole 104 allowing the insertion of a gas outlet end of the device to be disinfected; a gas distribution unit 200 including a first interface, a second interface, and a third interface that communicate with each other, the second interface being configured to communicate with a gas inlet end 601 of the device to be disinfected; an ozone generation unit 300 having an ozone outlet 301 communicating with the first interface, the ozone generation unit 300 including an ozone generator configured to generate ozone and a power apparatus configured to deliver the ozone to the first interface; a suction pump 400, the suction pump 400 having a suction port 401 and an exhaust port 402, the suction port 401 communicating with the third interface; a filter 500 having a plurality of exhaust holes 502 and at least one gas inlet 501, the gas inlet 501 of the filter 500 communicating with the exhaust port 402 of the suction pump 400; and a control module 700 configured to connect and control the operation of the ozone generation unit 300 and the suction pump 400.

In the present embodiment, the sealed disinfection space 102 is opened and closed in a drawer type. Specifically, referring to FIG. 1, FIG. 3, and FIG. 7, the ozone disinfection device 100 includes an outer box and an inner box. The outer box includes a top cover, a base 101, and a peripheral side wall connected between the top cover and the base 101. A front side of the peripheral side wall is provided with a mounting hole into which the inner box can be inserted. The inner box has an opening on its upper end, and internally has the sealed disinfection space 102. The through hole 104 is provided on a front side of the inner box. When the inner box is inserted into the outer box from the mounting hole, the opening on the upper end of the inner box is sealed. At this time, the sealed disinfection space 102 can only communicate with the outside through the through hole 104. That is, if the through hole 104 is blocked, gas in the sealed disinfection space 102 will not escape.

In some other embodiments, the sealed disinfection space 102 may also be opened and closed in a flip type. A specific structure will not be described in detail in the disclosure. It should be understood that this is also the technical solution claimed by the disclosure.

In the present embodiment, referring to FIG. 3, the ozone generation unit 300, the suction pump 400, and the filter 500 are all fixed to the base 101. The sealed disinfection space 102 is located on upper sides of the ozone generation unit 300, the suction pump 400, and the filter 500. Specifically, when the inner box is inserted into the outer box, the inner box is located just above the base 101, and the ozone generation unit 300, the suction pump 400, and the filter 500 are all located between the inner box and the base 101. By such design, an internal space of the outer box is fully utilized, making the entire ozone disinfection device 100 miniaturized and enhancing its portability.

In the present embodiment, referring to FIG. 3, the ozone generation unit 300 communicates with the first interface of the gas distribution unit 200 through a first pipeline 201. The suction port 401 of the suction pump 400 communicates with the third interface of the gas distribution unit 200 through a third pipeline 203. The exhaust port 402 of the suction pump 400 communicates with the gas inlet 501 of the filter 500 through a fourth pipeline 204. The second interface of the gas distribution unit 200 communicates with the gas inlet end 601 of the device to be disinfected through a second pipeline 202. Preferably, the material of the first pipeline 201, the second pipeline 202, the third pipeline 203, and the fourth pipeline 204 is silica gel.

In some other embodiments, the material of the first pipeline 201, the second pipeline 202, the third pipeline 203, and the fourth pipeline 204 may also be Ethylene Propylene Diene Monomer.

In the present embodiment, the gas distribution unit 200 is a three-way pipe.

Figure 4:
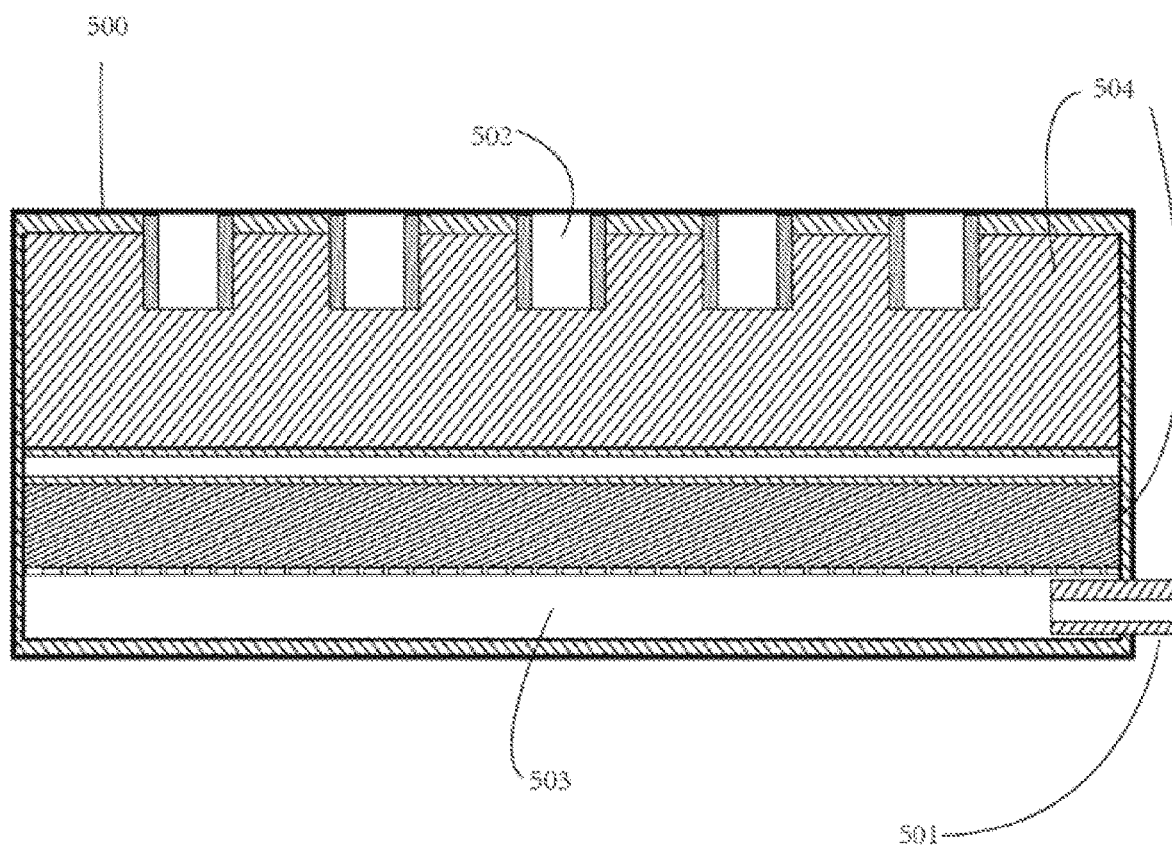
FIG. 4 is a schematic cross-sectional diagram of a filter of an ozone disinfection device provided in Embodiment I of the disclosure.

In the present embodiment, the filter 500 has the plurality of exhaust holes 502. Specifically, referring to FIG. 4, the filter 500 includes a hollow housing, the housing has the plurality of exhaust holes 502 and the gas inlet 501, the gas inlet 501 is provided on lower sides of the plurality of exhaust holes 502, at least one filter layer 504 is disposed between the gas inlet 501 and the exhaust holes 502, and the housing internally has a buffer cavity 503 that is located on a lower side of the lowermost filter layer 504 and communicates with the gas inlet 501 of the filter 500. Since the filter 500 has a plurality of exhaust holes 502, non-polluting gas generated by the catalytic decomposition of ozone may be expelled more quickly, thus improving the ventilation efficiency of the filter 500. In addition, considering that solid particles such as fine dust may be included in fast-flowing ozone gas, the buffer cavity 503 is designed inside the housing, which functions to collect the solid particles included in the ozone gas for centralized removal. Preferably, two filter layers 504 are disposed between the gas inlet 501 and the exhaust holes 502, and there is a gap between the two filter layers 504. Therefore, the catalytic ozone decomposition ability and efficiency of the filter 500 may be improved to ensure that no ozone is included in the gas expelled from the filter 500. Here, at least one of the filter layers 504 is filled with manganese-containing particulate matters for catalytic ozone decomposition, so the ozone flowing through the filter 500 is decomposed into non-toxic and non-polluting oxygen under the action of the particulate matters to ensure the sanitation and safety of the surrounding environment.

In some other embodiments, three or more filter layers 504 may be disposed in the housing, and a certain gap is maintained between two adjacent filter layers 504. The ozone flowing through the filter 500 flows in from the gas inlet 501 of the filter 500, sequentially passes through the plurality of filter layers 504, and then is expelled from the exhaust holes 502. The ozone may be completely decomposed into non-toxic and non-polluting oxygen after being catalytically decomposed by the plurality of filter layers 504. It should be noted that substances filled in each filter layer 504 may be the same, and of course, may be different, as long as they have the function of absorbing or catalyzing the decomposition of ozone.

In the present embodiment, the power apparatus is a positive pressure gas pump, so that the ozone generated by the ozone generator is quickly expelled into the second interface, that is, the ozone generated by the ozone generator does not enter the second interface through a slow diffusion process, thus improving the work efficiency of the entire ozone disinfection device 100.

Figure 2:
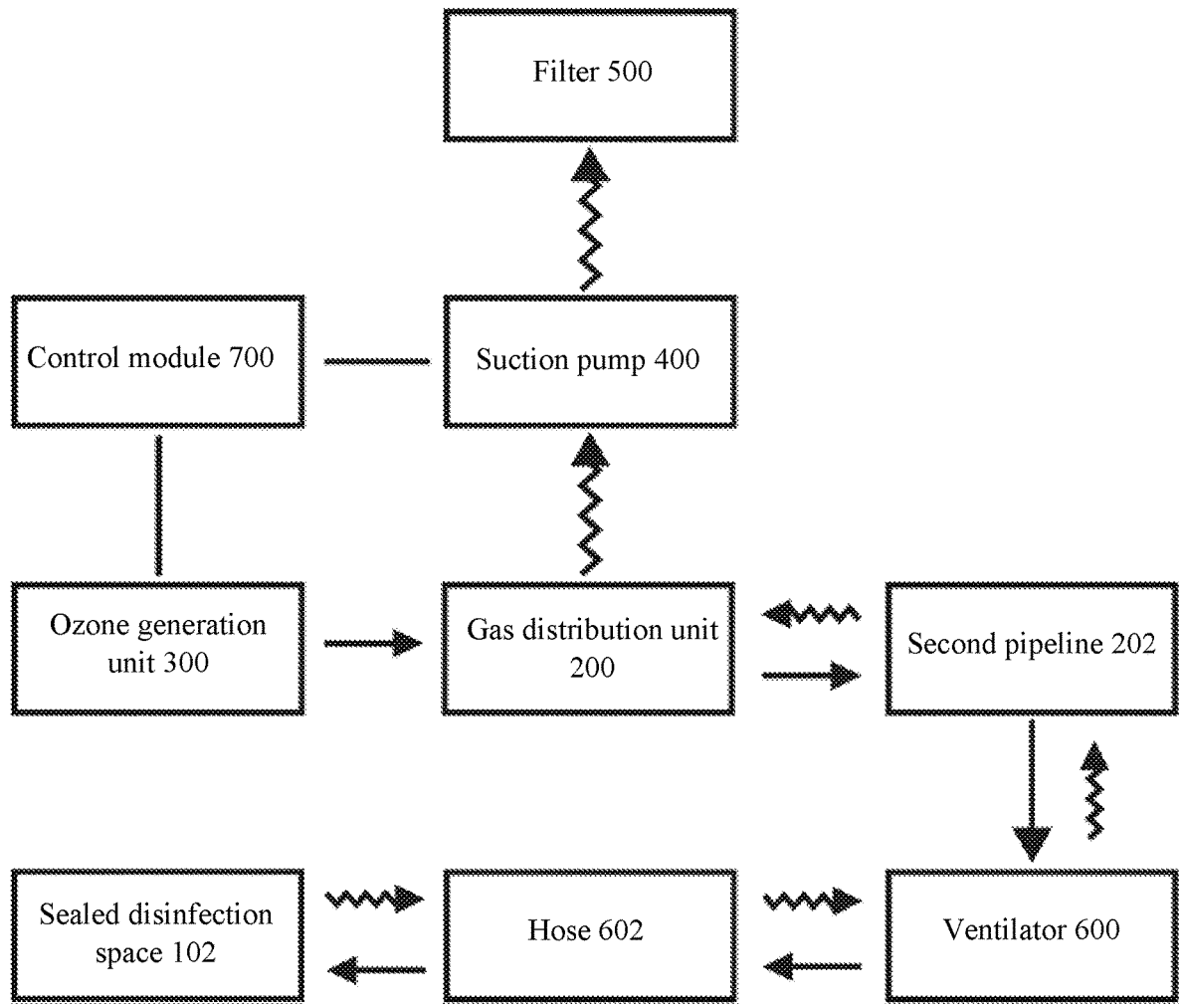
FIG. 2 is a schematic diagram of an ozone disinfection device provided in Embodiment I of the disclosure for disinfecting a ventilator, a hose, and a face mask, where straight arrows are a path of outputting ozone and disinfecting passing objects, and curved arrows are a path of pumping ozone back by a suction pump for filtration.

Referring to FIG. 1 and FIG. 2, when disinfecting the ventilator 600 and the face mask 603 and the hose 602 thereof using the ozone disinfection device 100, the ventilator 600 communicates with the second interface through the second pipeline 202, after the sealed disinfection space 102 is opened, the hose 602 is inserted into the sealed disinfection space 102 from the through hole 104, the face mask 603 is put into the sealed disinfection space 102, the ventilator 600, the hose 602, and the face mask 603 are connected in sequence, and then the sealed disinfection space 102 is closed. After the above operations are completed, the control module 700 activates the ozone generation unit 300, and ozone generated by the ozone generation unit 300 flows into the ventilator 600, the hose 602, the face mask 603, and the sealed disinfection space 102 in sequence through the gas distribution unit 200, thereby performing ozone disinfection treatment on the ventilator 600, the hose 602, and the face mask 603. After the disinfection is completed, the control module 700 controls the ozone generation unit 300 to stop working and activates the suction pump 400, the suction pump 400 generates a strong negative pressure, and pumps all the ozone remaining inside the sealed disinfection space 102, the face mask 603, the hose 602, and the ventilator 600 to the filter 500, and the filter 500 performs catalytic decomposition treatment on the ozone flowing through, and then evacuates, thereby eliminating the ozone remaining inside the sealed disinfection space 102, the ventilator 600, the hose 602, and the face mask 603, and protecting a user from inhaling the remaining ozone when using the disinfected ventilator 600, hose 602 and face mask 603 while not causing ozone pollution to the surrounding environment. The safety and environmental protection of the ozone disinfection device 100 are improved. Compared with the existing passive ozone disinfection technology, the ozone disinfection device has the advantages of higher efficiency, high speed, safety, and environmental protection.

Figure 5:
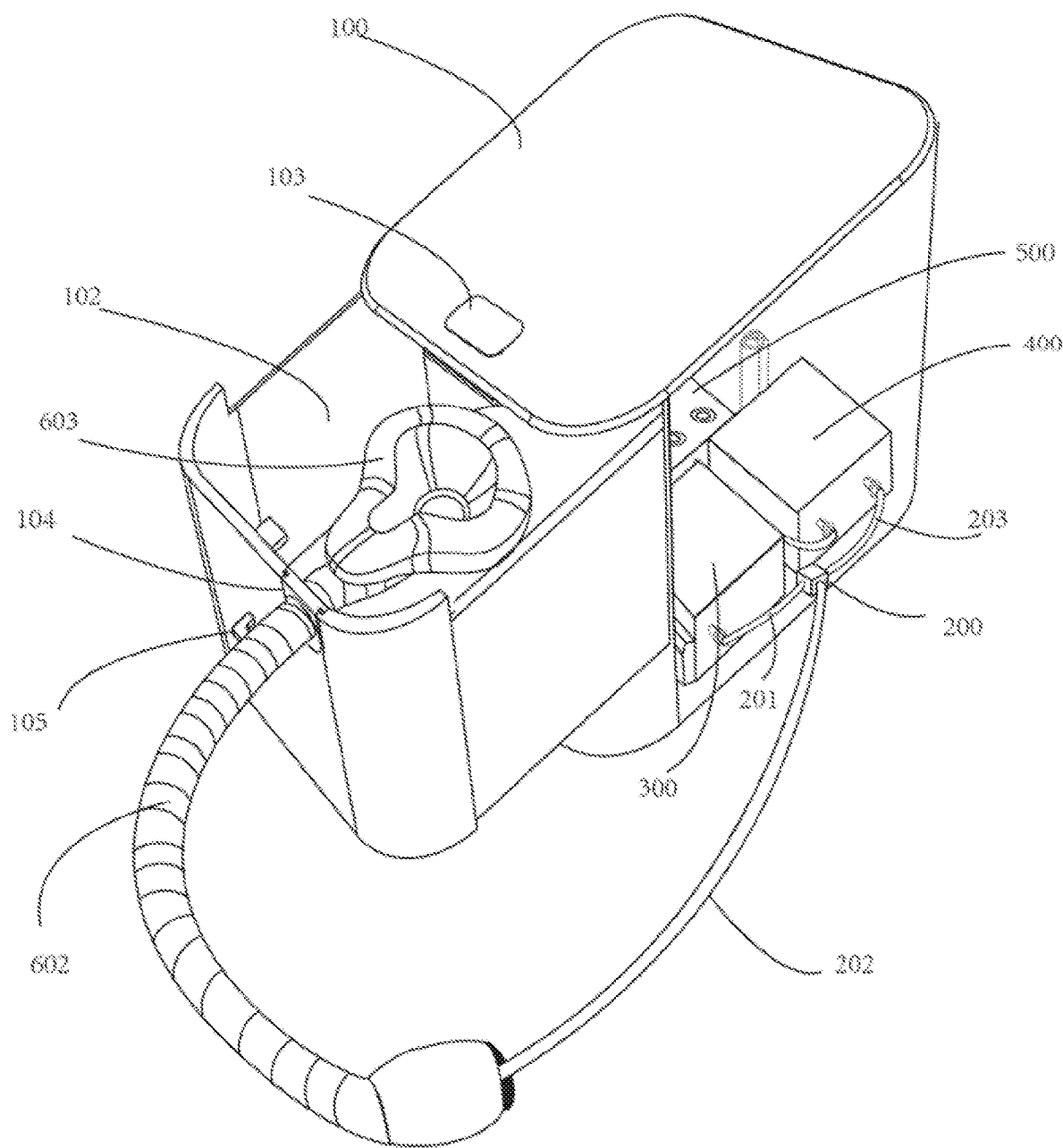
FIG. 5 is reference diagram (II) of a use state of an ozone disinfection device provided in Embodiment I of the disclosure, which illustrates a state in which the ozone disinfection device disinfects a hose and a face mask.
Figure 6:
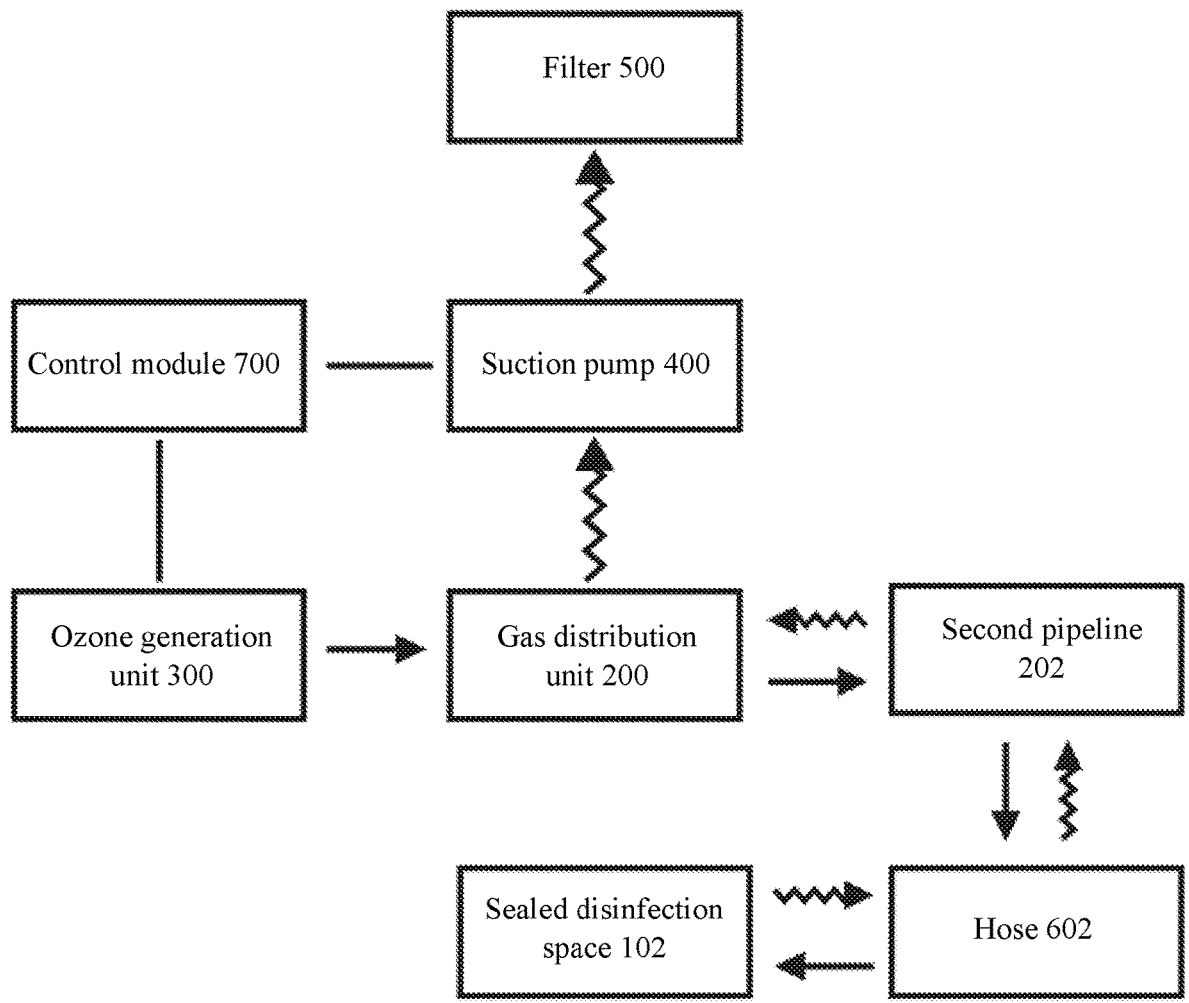
FIG. 6 is a schematic diagram of an ozone disinfection device provided in Embodiment I of the disclosure for disinfecting a hose and a face mask, where straight arrows are a path of outputting ozone and disinfecting passing objects, and curved arrows are a path of pumping ozone back by a suction pump for filtration.

Referring to FIG. 5 and FIG. 6, when disinfecting the face mask 603 and the hose 602 using the ozone disinfection device 100, the hose 602 communicates with the second interface through the second pipeline 202, after the sealed disinfection space 102 is opened, the hose 602 is inserted into the sealed disinfection space 102 from the through hole 104, the face mask 603 is put into the sealed disinfection space 102, the hose 602 and the face mask 603 are connected, and then the sealed disinfection space 102 is closed. After the above operations are completed, the control module 700 activates the ozone generation unit 300, and ozone generated by the ozone generation unit 300 flows into the hose 602, the face mask 603, and the sealed disinfection space 102 in sequence through the gas distribution unit 200, thereby performing ozone disinfection treatment on the hose 602 and the face mask 603. After the disinfection is completed, the control module 700 controls the ozone generation unit 300 to stop working and activates the suction pump 400, the suction pump 400 generates a strong negative pressure and pumps all the ozone remaining inside the sealed disinfection space 102, the face mask 603, and the hose 602 to the filter 500, and the filter 500 performs catalytic decomposition treatment on the ozone flowing through and then evacuates, thereby eliminating the ozone remaining inside the sealed disinfection space 102, the hose 602, and the face mask 603, and protecting a user from inhaling the remaining ozone when using the disinfected hose 602 and face mask 603 while not causing ozone pollution to the surrounding environment. The safety and environmental protection of the ozone disinfection device 100 are improved. Compared with existing passive ozone disinfection technologies, the ozone disinfection device has the advantages of higher efficiency, high speed, safety, and environmental protection.

After experimental tests, all the remaining ozone after disinfection may be quickly recycled and then safely treated through the ozone filter 500, realizing active elimination of the ozone remaining in the ventilator 600, the hose 602, and the sealed disinfection space 102. The characteristic of the disclosure is a technology of active ozone elimination. The characteristic of active ozone elimination is that the ozone disinfection device 100 may actively recycle all the remaining ozone generated, so that all these ozone may be filtered through the ozone filter 500 and catalytically decomposed into non-toxic and non-polluting gas, thereby achieving a safe and reliable effect. Unlike a passive technology in the prior art, the passive technology refers to placing the filter 500 at a certain position in a disinfection space and simply adsorbing ozone through the surface without an external force. The effect of the passive technology is not good and the efficiency is low, and only the ozone around the filter 500 can be simply adsorbed while the ozone remaining in other spaces such as the hose 602 cannot be effectively adsorbed.

In some other implementations, if the ozone generation unit 300 and the suction pump 400 are connected to the gas distribution unit 200 simultaneously, the situations where there is one or more interfaces of the gas distribution unit 200 for connection and delivery to the sealed disinfection space 102 fall within the scope of protection.

Further, the ozone disinfection device 100 is provided with an open button 103 and a handle 105. Referring to FIG. 7, the open button 103 is disposed on the top cover of the outer box, and the handle 105 is disposed on the front side of the inner box. The function of the open button 103 is to lock the inner box. When the open button 103 is pressed, the inner box is unlocked. The outer box may be drawn out by pulling the handle 105, thereby opening the sealed disinfection space 102.

Further, referring to FIG. 7, the control module 700 includes a display screen for displaying work progress and work content. The work progress includes a percentage of a total work time or a countdown of a work time. In this way, the user can better understand the work progress and work content of the ozone disinfection device 100.

Further, the control module 700 is configured to control the ozone generation unit 300 to output enough ozone so that the concentration of ozone in the sealed disinfection space 102 is not lower than a concentration value capable of killing conventional germs inside the ventilator. Therefore, it may be ensured that the ozone generation unit 300 generates enough ozone in the disinfection process, and it may be ensured that germs in the ventilator 600, the hose 602, and the face mask 603 can be completely killed.

Further, referring to FIG. 7, in order to facilitate the connection between the second pipeline 202 and the gas distribution unit 200, the second interface of the gas distribution unit 200 is designed to pass through the outer box.

Embodiment II

The present embodiment provides an ozone disinfection system. The system includes a ventilator 600, a hose 602, a face mask 603, and the ozone disinfection device provided in Embodiment I. The ventilator 600, the hose 602, and the face mask 603 communicate in sequence. A gas inlet end 601 of the ventilator 600 communicates with the second interface of the gas distribution unit 200 of the ozone disinfection device through a second pipeline 202. A gas outlet end of the hose 602 extends into the sealed disinfection space 102 from the through hole 104. The face mask 603 is received in the sealed disinfection space 102. Both the hose 602 and the face mask 603 are equipment matching the ventilator 600.

The control module 700 is configured to control the ozone generation unit 300 to output enough ozone so that the concentration of ozone in the sealed disinfection space 102 is not lower than a concentration value capable of killing conventional germs inside the ventilator.

In the present embodiment, the suction volume of the suction pump 400 is not lower than the exhaust volume of the ozone generation unit 300.

In the present embodiment, the sealed disinfection space 102 is opened and closed in a drawer type. Of course, in other embodiments, the sealed disinfection space may be opened and closed in a flip type.

In the present embodiment, the ozone generation unit 300 communicates with the first interface of the gas distribution unit 200 through a first pipeline 201, the suction port 401 of the suction pump 400 communicates with the third interface of the gas distribution unit 200 through a third pipeline 203, the exhaust port 402 of the suction pump 400 communicates with the gas inlet 501 of the filter 500 through a fourth pipeline 204, and the second interface of the gas distribution unit 200 communicates with the ventilator 600 through the second pipeline 202.

For the work principle, reference is made to the process of disinfecting the ventilator 600 and the face mask 603 and the hose 602 thereof using the ozone disinfection device 100 in Embodiment I.

Embodiment III

The present embodiment provides an ozone disinfection system. The ozone disinfection system includes a hose 602, a face mask 603, and the ozone disinfection device provided in Embodiment I. The hose 602 and the face mask 603 communicate with each other. A gas inlet end 601 of the hose 602 communicates with the second interface of the gas distribution unit 200 of the ozone disinfection device through a second pipeline 202. A gas outlet end of the hose 602 extends into the sealed disinfection space 102 from the through hole 104. The face mask 603 is received in the sealed disinfection space 102. Both the hose 602 and the face mask 603 are equipment matching a ventilator 600.

In the present embodiment, the control module 700 is configured to control the ozone generation unit 300 to output enough ozone so that the concentration of ozone in the sealed disinfection space 102 is not lower than a concentration value capable of killing conventional germs inside the ventilator.

In the present embodiment, the suction volume of the suction pump 400 is not lower than the exhaust volume of the ozone generation unit 300.

In the present embodiment, the sealed disinfection space 102 is opened and closed in a drawer type. Of course, in other embodiments, the sealed disinfection space may be opened and closed in a flip type.

In the present embodiment, the ozone generation unit 300 communicates with the first interface of the gas distribution unit 200 through a first pipeline 201, the suction port 401 of the suction pump 400 communicates with the third interface of the gas distribution unit 200 through a third pipeline 203, the exhaust port 402 of the suction pump 400 communicates with the gas inlet 501 of the filter 500 through a fourth pipeline 204, and the second interface of the gas distribution unit 200 communicates with the hose 602 through the second pipeline 202.

For the work principle, reference is made to the process of disinfecting the hose 602 and the face mask 603 using the ozone disinfection device 100 in Embodiment I.

Embodiment IV

The present embodiment provides an ozone disinfection method. The ozone disinfection method is implemented through the ozone disinfection device provided in Embodiment I.

In the present embodiment, the ozone disinfection method includes the following steps:

connecting a gas outlet end and a gas inlet end of a device to be disinfected to the sealed disinfection space 102 and the second interface, respectively;

activating, by the control module 700, the ozone generation unit 300, ozone generated by the ozone generation unit 300 flowing into the device to be disinfected and the sealed disinfection space 102 in sequence through the gas distribution unit 200; here, the ozone generation unit 300 outputs a certain amount of ozone so that the concentration of ozone in the sealed disinfection space 102 is not lower than a concentration value capable of killing conventional germs inside a ventilator;

controlling, by the control module 700, the ozone generation unit 300 to stop working and activating the suction pump 400, generating, by the suction pump 400, a strong negative pressure, and pumping all the ozone remaining inside the sealed disinfection space 102 and the device to be disinfected to the filter 500; and performing, by the filter 500, catalytic decomposition treatment on the ozone flowing through and then evacuating.

In the present embodiment, the device to be disinfected includes a ventilator 600, a hose 602, and a face mask 603. For the step of "connecting a gas outlet end and a gas inlet end of a device to be disinfected to the sealed disinfection space and the second interface, respectively," the specific process is as follows: the ventilator communicates with the second interface through the second pipeline 202, after the sealed disinfection space 102 is opened, the hose 602 is inserted into the sealed disinfection space 102 from the through hole 104, the face mask 603 is put into the sealed disinfection space 102, the ventilator 600, the hose 602, and the face mask 603 are connected in sequence, and then the sealed disinfection space 102 is closed.

In some other embodiments, the device to be disinfected may include only a hose 602 and a face mask 603. Here, for the step of "connecting a gas outlet end and a gas inlet end of a device to be disinfected to the sealed disinfection space and the second interface, respectively," the specific process is as follows: the hose 602 communicates with the second interface through the second pipeline 202, after the sealed disinfection space 102 is opened, the hose 602 is inserted into the sealed disinfection space 102 from the through hole 104, the face mask 603 is put into the sealed disinfection space 102, the hose 602 and the face mask 603 are connected, and then the sealed disinfection space 102 is closed.

The above is only optional embodiments of the disclosure and does not limit the patent scope of the disclosure accordingly. Any equivalent structural transformation made by using the specification and drawings of the disclosure under the creative concept of the disclosure, or direct/indirect application in other related technical fields is included in the patent protection scope of the disclosure.

The invention claimed is:

1. An ozone disinfection device, comprising:
   a sealed disinfection space configured to receive a device to be disinfected or temporarily store ozone, the sealed disinfection space communicating with a through hole for allowing the insertion of a gas outlet end of the device to be disinfected;
   a gas distribution unit comprising a first interface, a second interface, and a third interface that communicate with each other, the second interface being configured to communicate with a gas inlet end of the device to be disinfected;
   an ozone generation unit having an ozone outlet communicating with the first interface;
   a suction pump having a suction port and an exhaust port, the suction port communicating with the third interface;
   a filter communicating with the suction pump; and
   a control module configured to connect and control the operation of the ozone generation unit and the suction pump,
   wherein the filter comprises a housing that comprises a plurality of exhaust holes and at least one gas inlet, wherein the gas inlet communicates with the exhaust port of the suction pump.

2. The ozone disinfection device according to claim 1, wherein the filter comprises a gas inlet, and at least one filter layer that is disposed between the gas inlet and the plurality of exhaust holes, and the housing internally has a buffer cavity that is located on a lower side of a lowermost filter layer and communicates with the gas inlet.

3. The ozone disinfection device according to claim 2, wherein at least two filter layers are disposed between the gas inlet and the plurality of exhaust holes, and there is a gap between each two adjacent filter layers.

4. The ozone disinfection device according to claim 3, wherein at least one of the filter layers is filled with manganese-containing particulate matters for catalytic ozone decomposition.

5. The ozone disinfection device according to claim 1, wherein the sealed disinfection space is opened and closed in a flip type or a drawer type.

6. The ozone disinfection device according to claim 1, wherein the control module comprises a display screen for displaying work progress and work content; wherein the work progress comprises a percentage of a total work time or a countdown of a work time.

7. The ozone disinfection device according to claim 1, wherein the gas inlet is provided on lower sides of the plurality of exhaust holes.

8. The ozone disinfection device according to claim 1, wherein the ozone disinfection device includes an outer box and an inner box; wherein the outer box includes a top cover, a base, and a peripheral side wall connected between the top cover and the base, a front side of the peripheral side wall is provided with a mounting hole into which the inner box can be inserted; the inner box has an opening on its upper end, and internally has the sealed disinfection space.

9. The ozone disinfection device according to claim 8, wherein the ozone disinfection device is provided with an open button and a handle; wherein the open button is disposed on the top cover of the outer box, and the handle is disposed on the front side of the inner box; wherein the open button is to lock the inner box, while the outer box can be drawn out by pulling the handle, thereby opening sealed disinfection space.

10. The ozone disinfection device according to claim 1, wherein the ozone generation unit comprises an ozone generator configured to generate ozone and a power apparatus configured to deliver the ozone to the first interface.

11. The ozone disinfection device according to claim 1, wherein the ozone generation unit communicates with the first interface of the gas distribution unit through a first pipeline, the suction port of the suction pump communicates with the third interface of the gas distribution unit through a third pipeline, the exhaust port of the suction pump communicates with the gas inlet of the filter through a fourth pipeline, and the second interface of the gas distribution unit communicates with the gas inlet end of the device to be disinfected through a second pipeline.

12. The ozone disinfection device according to claim 1, wherein the control module is configured to control the ozone generation unit to output enough ozone so that the concentration of ozone in the sealed disinfection space is not lower than a concentration value capable of killing conventional germs inside a ventilator.

13. The ozone disinfection device according to claim 1, wherein a suction volume of the suction pump is not lower than an exhaust volume of the ozone generation unit.

14. An ozone disinfection system, comprising: a ventilator, a hose, a face mask, and an ozone disinfection device;
   wherein the ozone disinfection device comprises:
   a sealed disinfection space communicating with a through hole;

a gas distribution unit comprising a first interface, a second interface, and a third interface that communicate with each other;

an ozone generation unit having an ozone outlet communicating with the first interface;

a suction pump having a suction port and an exhaust port, the suction port communicating with the third interface;

a filter communicating with the suction pump; and a control module configured to connect and control the operation of the ozone generation unit and the suction pump;

wherein the ventilator, the hose, and the face mask communicate in sequence;

a gas inlet end of the ventilator communicates with the second interface of the gas distribution unit of the ozone disinfection device through a second pipeline;

a gas outlet end of the hose extends into the sealed disinfection space from the through hole; and the face mask is received in the sealed disinfection space, and wherein the filter comprises a housing that comprises a plurality of exhaust holes and at least one gas inlet, wherein the gas inlet communicates with the exhaust port of the suction pump.

15. The ozone disinfection system according to claim 14, wherein the filter comprises a gas inlet, and at least one filter layer that is disposed between the gas inlet and the plurality of exhaust holes, and the housing internally has a buffer cavity that is located on a lower side of a lowermost filter layer and communicates with the gas inlet.

16. The ozone disinfection system according to claim 14, wherein the ozone generation unit communicates with the first interface of the gas distribution unit through a first pipeline, the suction port of the suction pump communicates with the third interface of the gas distribution unit through a third pipeline, the exhaust port of the suction pump communicates with the gas inlet of the filter through a fourth pipeline.

17. An ozone disinfection system, comprising: a hose, a face mask, and an ozone disinfection device;

wherein the ozone disinfection device comprises:

a sealed disinfection space communicating with a through hole;

a gas distribution unit comprising a first interface, a second interface, and a third interface that communicate with each other;

an ozone generation unit having an ozone outlet communicating with the first interface;

a suction pump having a suction port and an exhaust port, the suction port communicating with the third interface;

a filter communicating with the suction pump; and a control module configured to connect and control the operation of the ozone generation unit and the suction pump;

wherein the hose and the face mask communicate with each other;

a gas inlet end of the hose communicates with the second interface of the gas distribution unit of the ozone disinfection device through a second pipeline;

a gas outlet end of the hose extends into the sealed disinfection space from the through hole; and the face mask is received in the sealed disinfection space, and wherein the filter comprises a housing that comprises a plurality of exhaust holes and at least one gas inlet, wherein the gas inlet communicates with the exhaust port of the suction pump.

18. The ozone disinfection system according to claim 17, wherein the filter comprises a gas inlet, and at least one filter layer is disposed between the gas inlet and the plurality of exhaust holes, and the housing internally has a buffer cavity that is located on a lower side of a lowermost filter layer and communicates with the gas inlet.

19. The ozone disinfection system according to claim 17, wherein the ozone generation unit communicates with the first interface of the gas distribution unit through a first pipeline, the suction port of the suction pump communicates with the third interface of the gas distribution unit through a third pipeline, the exhaust port of the suction pump communicates with the gas inlet of the filter through a fourth pipeline.

* * * * *